(12) United States Patent
Kaltenbach et al.

(10) Patent No.: US 6,617,310 B2
(45) Date of Patent: Sep. 9, 2003

(54) PHOSPHATE ESTERS OF BIS-AMINO ACID SULFONAMIDES CONTAINING SUBSTITUTED BENZYL AMINES

(75) Inventors: Robert F. Kaltenbach, Wilmington, DE (US); George L. Trainor, Wilmington, DE (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 09/908,431

(22) Filed: Jul. 18, 2001

(65) Prior Publication Data

US 2002/0028791 A1 Mar. 7, 2002

Related U.S. Application Data

(60) Provisional application No. 60/219,399, filed on Jul. 19, 2000.

(51) Int. Cl.[7] .......................... A61K 31/18; A61K 31/36; A61K 31/34; C07D 317/44; C07C 303/60
(52) U.S. Cl. .......................... 514/18; 514/19; 514/466; 514/469; 514/603; 536/330; 536/331; 549/361; 549/438; 549/462; 564/86
(58) Field of Search ................................. 549/361, 438, 549/462; 514/18, 19, 466, 469, 603; 564/86; 536/330, 331

(56) References Cited

U.S. PATENT DOCUMENTS 6,150,556 A    11/2000  Getman et al.
6,391,919 B1 *  5/2002  Kaltenbach et al. ........ 514/603

FOREIGN PATENT DOCUMENTS

| WO | 9404492 | 3/1994 |
| WO | 9405639 | 3/1994 |
| WO | 9506030 | 3/1995 |
| WO | 9533464 | 12/1995 |
| WO | 9628464 | 9/1996 |
| WO | WO 9933792 | 7/1999 |
| WO | 0042060 | 7/2000 |

* cited by examiner

*Primary Examiner*—Alan L. Rotman
*Assistant Examiner*—Raymond Covington
(74) *Attorney, Agent, or Firm*—Mary K. VanAtten

(57) ABSTRACT

This invention relates generally to phosphate esters of bis-amino acid sulfonamides containing substituted benzyl amines of formula I:

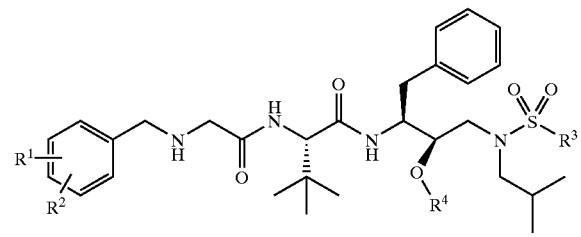

or stereoisomeric forms, stereoisomeric mixtures, or pharmaceutically acceptable salt forms thereof, which are useful as HIV protease inhibitors, pharmaceutical compositions comprising the same, and methods of using the same for treating viral infection.

30 Claims, No Drawings

PHOSPHATE ESTERS OF BIS-AMINO ACID SULFONAMIDES CONTAINING SUBSTITUTED BENZYL AMINES

This application claims benefit of 06/219,399, filed Jul. 19, 2000.

Inhibitors and are disclosed in U.S. Ser. No. 09/482,146, filed Jan. 12, 2000 now U.S. Pat. No. 6,391,919, the contents of which are hereby incorporated by reference.

FIELD OF THE INVENTION

This invention relates generally to phosphate esters of bis-amino acid sulfonamides containing substituted benzyl amines, pharmaceutical compositions comprising the same, and methods of using the same for treating viral infection.

BACKGROUND OF THE INVENTION

Compounds of Formula A are known HIV Protease

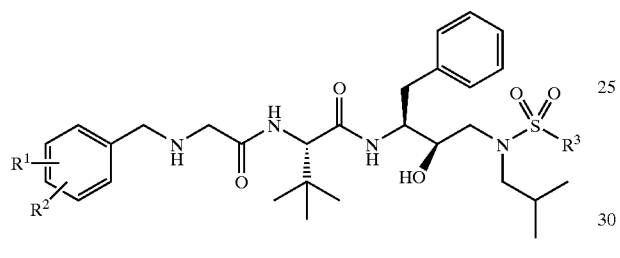

A

In the above formula, $R^1$ is F, $R^2$ is F or H, and $R^3$ is selected from the group: 4-aminophenyl, 3-aminophenyl, 2,3-dihydrobenzofuran-5-yl, and 1,3-benzodioxol-5-yl. The presence of the hydroxyl group in Formula A is expected to contribute to variable plasma levels following oral administration of these compounds. Since consistent plasma levels following oral administration are a desirable characteristic of drugs, it is desirable to discover new compounds that address the potential plasma level variability of the compounds of Formula A.

SUMMARY OF THE INVENTION

Accordingly, one object of the present invention is to provide novel HIV protease inhibitors.

It is another object of the present invention to provide a novel method for treating HIV infection which comprises administering to a host in need of such treatment a therapeutically effective amount of at least one of the compounds of the present invention or a pharmaceutically acceptable salt form thereof.

It is another object of the present invention to provide a novel method for treating HIV infection which comprises administering to a host in need thereof a therapeutically effective combination of (a) one of the compounds of the present invention and (b) one or more compounds selected form the group consisting of HIV reverse transcriptase inhibitors and HIV protease inhibitors.

It is another object of the present invention to provide pharmaceutical compositions with protease inhibiting activity comprising a pharmaceutically acceptable carrier and a therapeutically effective amount of at least one of the compounds of the present invention or a pharmaceutically acceptable salt form thereof.

It is another object of the present invention to provide novel HIV protease inhibitors for use in therapy.

It is another object of the present invention to provide the use of novel HIV protease inhibitors for the manufacture of a medicament for the treatment of a HIV.

It is another object of the present invention to provide a method of inhibiting HIV present in a body fluid sample that comprises treating the body fluid sample with an effective amount of a compound of the present invention.

It is another object of the present invention to provide a kit or container containing at least one of the compounds of the present invention in an amount effective for use as a standard or reagent in a test or assay for determining the ability of a potential pharmaceutical to inhibit HIV protease, HIV growth, or both.

These and other objects, which will become apparent during the following detailed description, have been achieved by the inventors' discovery that compounds of Formula I:

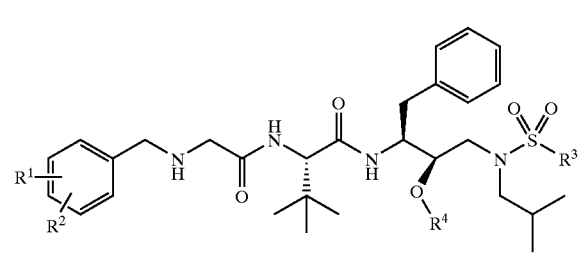

I wherein $R^1$, $R^2$, $R^3$, and $R^4$ are defined below, stereoisomeric forms, mixtures of stereoisomeric forms, or pharmaceutically acceptable salt forms thereof, are expected to be prodrugs of HIV protease inhibitors.

DETAILED DESCRIPTION OF PREFERRED EMBODIMENTS

[1] Thus, in an embodiment, the present invention provides a novel compound of Formula I:

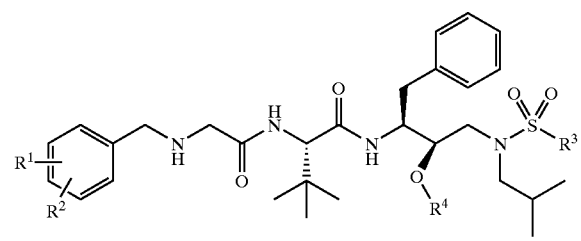

I or a pharmaceutically acceptable salt form thereof, wherein:

$R^1$ is F or H;

$R^2$ is F or H;

$R^3$ is selected from the group: 4-aminophenyl, 3-aminophenyl, 2,3-dihydrobenzofuran-5-yl, and 1,3-benzodioxol-5-yl; and, $R^4$ is selected from the group $PO_3H_2$, $PO_3HNa$, $PO_3HK$, $PO_3Na_2$, and $PO_3K_2$.

[2] In a preferred embodiment, the present invention provides a novel compound of Formula II:

II

[3] In another preferred embodiment, the present invention provides a novel compound of Formula IIa:

IIa

[4] In another preferred embodiment, the present invention provides a novel compound of Formula IIa, wherein:
  $R^3$ is 3-aminophenyl.
[5] In another preferred embodiment, the present invention provides a novel compound of Formula IIa, wherein:
  $R^3$ is 4-aminophenyl.
[6] In another preferred embodiment, the present invention provides a novel compound of Formula IIa, wherein:
  $R^3$ is 2,3-dihydrobenzofuran-5-yl or 1,3-benzodioxol-5-yl.
[7] In another preferred embodiment, the present invention provides a novel compound of Formula IIb:

IIb

[8] In another preferred embodiment, the present invention provides a novel compound of Formula IIb, wherein:
  $R^3$ is 3-aminophenyl.
[9] In another preferred embodiment, the present invention provides a novel compound of Formula IIb, wherein:
  $R^3$ is 4-aminophenyl.
[10] In another preferred embodiment, the present invention provides a novel compound of Formula IIb, wherein:
  $R^3$ is 2,3-dihydrobenzofuran-5-yl or 1,3-benzodioxol-5-yl.
[11] In another preferred embodiment, the present invention provides a novel compound of Formula IIc:

IIc

[12] In another preferred embodiment, the present invention provides a novel compound of Formula IIc, wherein:
  $R^3$ is 3-aminophenyl.
[13] In another preferred embodiment, the present invention provides a novel compound of Formula IIc, wherein:
  $R^3$ is 4-aminophenyl.
[14] In another preferred embodiment, the present invention provides a novel compound of Formula IIc, wherein:
  $R^3$ is 2,3-dihydrobenzofuran-5-yl or 1,3-benzodioxol-5-yl.
[15] In another preferred embodiment, the present invention provides a novel compound of Formula III:

III

[16] In another preferred embodiment, the present invention provides a novel compound of Formula IIIa:

IIIa

[17] In another preferred embodiment, the present invention 5 provides a novel compound of Formula IV:

IV

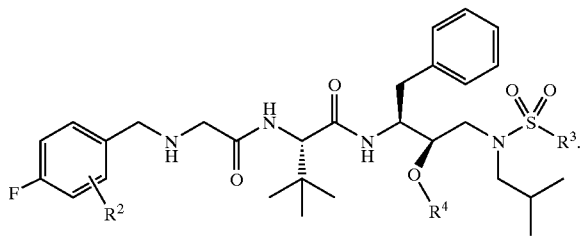

[18] In another preferred embodiment, the present invention provides a novel compound of Formula IVa:

IVa

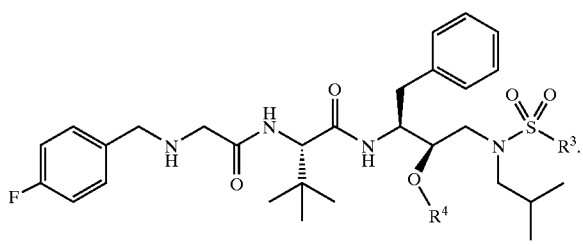

In another embodiment, the present invention provides a novel pharmaceutical composition comprising a pharmaceutically acceptable carrier and a therapeutically effective amount of a compound of formula I or pharmaceutically acceptable salt form thereof.

In another embodiment, the present invention provides a novel method for treating HIV infection that comprises administering to a host in need of such treatment a therapeutically effective amount of a compound of formula I or pharmaceutically acceptable salt form thereof.

In another embodiment, the present invention provides a novel method of treating HIV infection which comprises administering, in combination, to a host in need thereof a therapeutically effective amount of:
  (a) a compound of formula I; and,
  (b) at least one compound selected from the group consisting of HIV reverse transcriptase inhibitors and HIV protease inhibitors.

In another preferred embodiment, the reverse transcriptase inhibitor is selected from the group AZT, ddC, ddI, d4T, 3TC, delavirdine, efavirenz, nevirapine, Ro 18,893, trovirdine, MKC-442, HBY 097, ACT, UC-781, UC-782, RD4-2025, and MEN 10979, and the protease inhibitor is selected from the group saquinavir, ritonavir, indinavir, amprenavir, nelfinavir, palinavir, BMS-232623, GS3333, KNI-413, KNI-272, LG-71350, CGP-61755, PD 173606, PD 177298, PD 178390, PD 178392, U-140690, and ABT-378.

In an even more preferred embodiment, the reverse transcriptase inhibitor is selected from the group AZT, efavirenz, and 3TC and the protease inhibitor is selected from the group saquinavir, ritonavir, nelfinavir, and indinavir.

In a still further preferred embodiment, the reverse transcriptase inhibitor is AZT.

In another still further preferred embodiment, the protease inhibitor is ritonavir.

In another preferred embodiment, component (b) is a HIV reverse transcriptase inhibitor and a HIV protease inhibitor.

In another preferred embodiment, component (b) is two different HIV reverse transcriptase inhibitors.

In another embodiment, the present invention provides a pharmaceutical composition useful for the treatment of HIV infection, which comprises a therapeutically effective amount of:
  (a) a compound of formula I; and,
  (b) at least one compound selected from the group consisting of HIV reverse transcriptase inhibitors and HIV protease inhibitors, in one or more sterile containers.

In another embodiment, the present invention provides novel HIV protease inhibitors for use in therapy.

In another embodiment, the present invention provides the use of novel HIV protease inhibitors for the manufacture of a medicament for the treatment of a HIV.

DEFINITIONS

As used herein, the following terms and expressions have the indicated meanings. It will be appreciated that the compounds of the present invention contain asymmetrically substituted carbon atoms, and may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

The processes of the present invention are contemplated to be practiced on at least a multigram scale, kilogram scale, multikilogram scale, or industrial scale. Multigram scale, as used herein, is preferably the scale wherein at least one starting material is present in 10 grams or more, more preferably at least 50 grams or more, even more preferably at least 100 grams or more. Multikilogram scale, as used herein, is intended to mean the scale wherein more than one kilogram of at least one starting material is used. Industrial scale as used herein is intended to mean a scale which is other than a laboratory scale and which is sufficient to supply product sufficient for either clinical tests or distribution to consumers.

The present invention is intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

As used herein, "HIV reverse transcriptase inhibitor" is intended to refer to both nucleoside and non-nucleoside inhibitors of HIV reverse transcriptase (RT). Examples of nucleoside RT inhibitors include, but are not limited to, AZT, ddC, ddI, d4T, and 3TC. Examples of non-nucleoside RT inhibitors include, but are not limited to, delavirdine (Pharmacia and Upjohn, U90152S), efavirenz (DuPont), nevirapine (Boehringer Ingelheim), Ro 18,893 (Roche), trovirdine (Lilly), MKC-442 (Triangle), HBY 097 (Hoechst), HBY 1293 (Hoechst), ACT (Korean Research Institute), UC-781 (Rega Institute), UC-782 (Rega Institute), RD4-2025 (Tosoh Co. Ltd.), and MEN 10979 (Menarini Farmaceutici).

As used herein, "HIV protease inhibitor" is intended to refer to compounds that inhibit HIV protease. Examples include, but are not limited, saquinavir (Roche, Ro31-8959), ritonavir (Abbott, ABT-538), indinavir (Merck, MK-639), amprenavir (Vertex/Glaxo Wellcome), nelfinavir (Agouron, AG-1343), palinavir (Boehringer Ingelheim), BMS-232623 (Bristol-Myers Squibb), GS3333 (Gilead Sciences), KNI-413 (Japan Energy), KNI-272 (Japan Energy), LG-71350 (LG Chemical), CGP-61755 (Ciba-Geigy), PD 173606 (Parke Davis), PD 177298 (Parke Davis), PD 178390 (Parke Davis), PD 178392 (Parke Davis), tipranavir (Pharmacia and Upjohn, U-140690), DMP-450 (DuPont) and ABT-378.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

"Prodrugs" are intended to include any covalently bonded carriers that release the active parent drug according to formula (I) or other formulas or compounds of the present invention in vivo when such prodrug is administered to a mammalian subject. Prodrugs of a compound of the present invention, for example formula (I), are prepared by modifying functional groups present in the compound in such a way that the modifications are cleaved, either in routine manipulation or in vivo, to the parent compound. Prodrugs include compounds of the present invention wherein the amino group is bonded to any group that, when the prodrug is administered to a mammalian subject, cleaves to form a free amino. Examples of prodrugs include, but are not limited to, acetate, formate and benzoate derivatives of alcohol and amine functional groups in the compounds of the present invention, and the like.

"Stable compound" and "stable structure" are meant to indicate a compound that is sufficiently robust to survive isolation to a useful degree of purity from a reaction mixture, and formulation into an efficacious therapeutic agent. Only stable compounds are contemplated by the present invention.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

"Therapeutically effective amount" is intended to include an amount of a compound of the present invention or an amount of the combination of compounds claimed effective to inhibit HIV infection or treat the symptoms of HIV infection in a host. The combination of compounds is preferably a synergistic combination. Synergy, as described for example by Chou and Talalay, Adv. Enzyme Regul. 22:27–55 (1984), occurs when the effect (in this case, inhibition of HIV replication) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

One diastereomer of a compound of Formula I may display superior activity compared with the other. When required, separation of the racemic material can be achieved by HPLC using a chiral column or by a resolution using a resolving agent such as camphonic chloride as in Thomas J. Tucker, et al, *J. Med. Chem.* 1994, 37, 2437–2444. A chiral compound of Formula I may also be directly synthesized using a chiral catalyst or a chiral ligand, e.g. Mark A. Huffman, et al, *J. Org. Chem.* 1995, 60, 1590–1594.

Other features of the invention will become apparent in the course of the following descriptions of exemplary embodiments that are given for illustration of the invention and are not intended to be limiting thereof.

EXAMPLES

Abbreviations used in the Examples are defined as follows: "° C." for degrees Celsius, "d" for doublet, "dd" for doublet of doublets, "eq" for equivalent or equivalents, "g" for gram or grams, "mg" for milligram or milligrams, "mL" for milliliter or milliliters, "H" for hydrogen or hydrogens, "h" for hour or hours, "m" for multiplet, "M" for molar, "min" for minute or minutes, "MHz" for megahertz, "MS" for mass spectroscopy, "nmr" or "NMR" for nuclear magnetic resonance spectroscopy, "t" for triplet, and "TLC" for thin layer chromatography.

Example 1
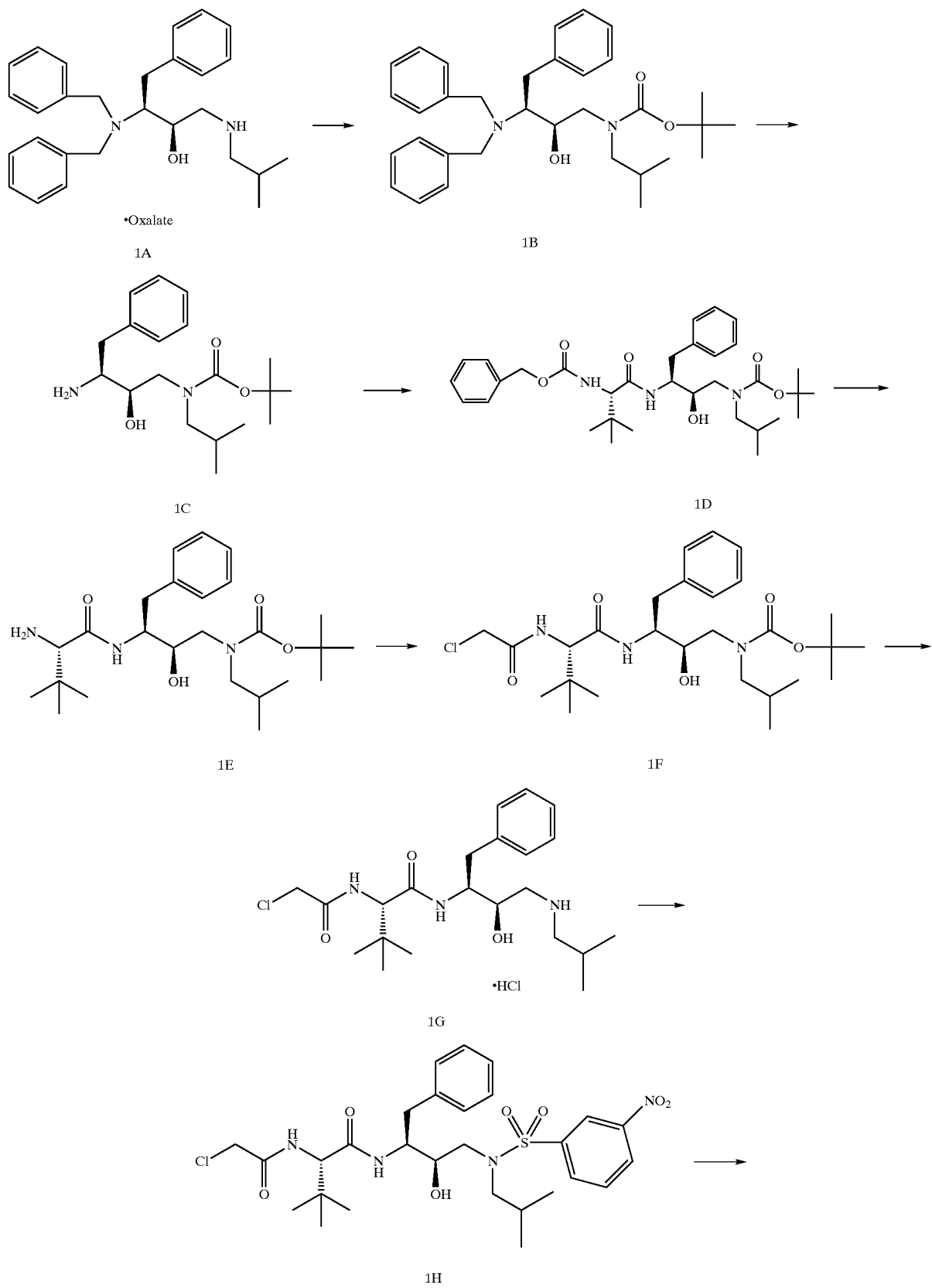

-continued

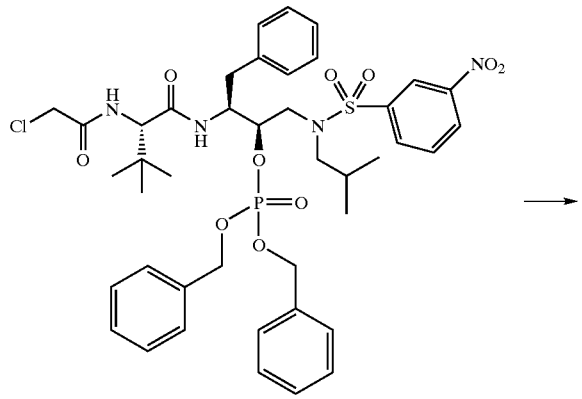

1I

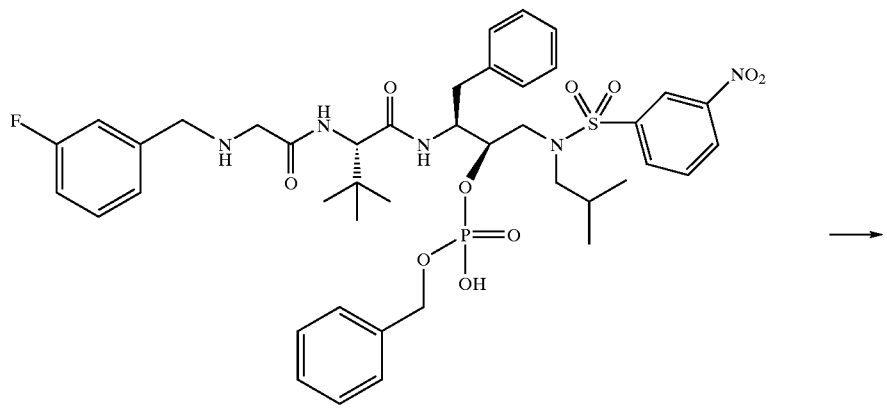

1J

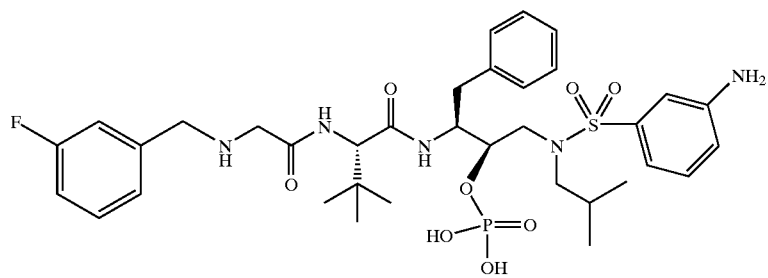

1

1B To a solution of N-[3(S)-[N,N-bis(phenylmethyl)amino]-2(R)-hydroxy-4-phenylbutyl]-N-isobutylamine.oxalic acid salt 1A (127.6 g, 251 mmol) in toluene (1 L), water (500 mL) and CH$_2$Cl$_2$ (400 mL) was added NaOH (50% aqueous, 44.5 g). After stirring 10 min the reaction mixture was extracted with toluene. The combined organic layers were washed with brine, dried (MgSO$_4$) and the solvent was removed under reduced pressure. The residue was taken up in THF (1 L), cooled to 0° C., and was treated with triethylamine (28.15 g, 278 mmol) and di-tert-butyl dicarbonate (55.23 g, 253 mmol). The solution was warmed to room temperature and was stirred overnight. The solvent was removed under reduced pressure and the residue was taken up in EtOAc (1 L), washed with water, 5% citric acid, water, saturated NaHCO$_3$, brine, and was dried (MgSO$_4$). The solvent was removed under reduced pressure to give the carbamate 1B that was used directly without further purification. CIMS (NH$_3$) m/z: 517 (M+H$^+$, 100%).

1C To a solution of crude 1B (251 mmol approx.) in methanol (500 mL) was added palladium hydroxide on carbon (20%, 10 g). The suspension was placed in a Parr bottle and was charged with hydrogen (55 psi). After shaking overnight the reaction mixture was filtered through Celite® and the solvent was removed under reduced pressure. The resulting solid was recrystallized (EtOAc/hexane) to give the amine 1C as a white solid (56.6 g, 67% (2 steps)). CIMS (NH$_3$) m/z: 337 (M+H$^+$, 100%).

1D To a solution of N-carbobenzyloxy-L-tert-leucine (47.5 g, 179 mmol) in DMF (250 mL) at 0° C. was added N-hydroxybenzotriazole (38.6 g, 285 mmol) and EDC (35.7 g, 186 mmol). After stirring 1.5h the solution was added to a suspension of 1C (56.6 g, 167 mmol) and 4-methylmorpholine (52.9 g, 521 mmol) in DMF (200 mL). The reaction mixture was allowed to warm to room temperature. After stirring overnight N,N-dimethylethylenediamine (4 mL) was added, the solution was stirred 1.5 h and the solvent was removed under reduced pressure. The residue was taken up in EtOAc (1 L), washed with water, 5% citric acid, water, saturated NaHCO$_3$, brine, and was dried (MgSO$_4$). The solvent was removed under reduced pressure to give 1D (97.5 g, 100%) that was used without further purification. CIMS (NH$_3$) m/z: 584 (M+H$^+$, 100%).

1E To a solution of 1D (97.5 g, 167 mmol) in methanol (300 mL) was added palladium hydroxide on carbon (20%, 10 g). The suspension was placed in a Parr bottle and was charged with hydrogen (55 psi). After shaking overnight the reaction mixture was filtered through Celite® and the solvent was removed under reduced pressure. The resulting solid was recrystallized (EtOAc/hexane) to give the amine 1E as a white solid (72.8 g, 97%). CIMS (NH$_3$) m/z: 450 (M+H$^+$, 100%).

1F To a solution of amine 1E (43.8 g, 97.6 mmol) in EtOAc (400 mL) and water (270 mL) was added KHCO$_3$ (27.7 g, 276 mmol) and chloroacetyl chloride (12.4 g, 111 mmol). After stirring 3 h, EtOAc (1 L) was added and the solution was washed with water, 5% citric acid, water, saturated NaHCO$_3$, brine, and was dried (MgSO$_4$). The solvent was removed under reduced pressure to give 1F as a white solid (51.0 g, 99%). CIMS (NH$_3$) m/z: 526 (M+H$^+$, 100%).

1G To a solution of 1F (33.8 g, 64.2 mmol) in EtOAc (600 mL) was added 4N HCl in dioxane (80 mL, 320 mmol) and the reaction mixture was stirred 6 h. The solvent was removed under reduced pressure and the resulting solid was triturated with cold ether to give the hydrochloride salt 1G (28.75 g, 97%). CIMS (NH$_3$) m/z: 426 (M+H$^+$, 100%).

1H To a solution of the salt 1G (28.8 g, 62.1 mmol) in THF (300 mL) and water (400 mL) was added K$_2$CO$_3$ (51.4 g, 370 mmol) and 3-nitrobenzenesulfonyl chloride (15.14 g, 68.3 mmol). After stirring 4 h, water was added and the suspension was extracted with EtOAc. The combined organic layers were washed with brine, 5% citric acid, water, saturated NaHCO$_3$, brine, and was dried (MgSO$_4$). The solvent was removed under reduced pressure and the resulting solid was triturated with EtOAc and hexane to give the sulfonamide IH as a white solid (32.1 g, 85%). CIMS (NH$_3$) m/z: 611 (M+H$^+$, 100%).

1I To a solution of N-[2R-hydroxy-3-[[(3-nitrophenyl)sulfonyl](2-methylpropyl)amino]-1S-(phenylmethyl)propyl]-2S-[(chloroacetyl)amino]-3,3-dimethylbutanamide 1H (2.20 g, 3.59 mmol) in THF (13 mL) was added 1H-tetrazole (400 mg, 5.70 mmol) and dibenzyl diisopropylphosphoramidite (1.64 g, 4.76 mmol). After stirring 4 h the reaction mixture was cooled to 0° C. and water (1.75 mL) and 30% aqueous hydrogen peroxide (1.75 mL) was added. After stirring 45 min the mixture was diluted with EtOAc and was washed with water, sat. NaHSO$_3$, water, brine, and was dried (MgSO$_4$). The solvent was removed under reduced pressure and the residue was chromatographed (silica gel, 5% methanol/CH$_2$Cl$_2$) to give the phosphate 1I as a white solid (2.79 g, 89%). ESI m/z: 869 (M−H$^-$).

1J To a solution of chloride 1I (642 mg, 0.53 mmol) in THF (4 mL) was added 3-fluorobenzylamine (510 mg, 4.1 mmol) and the reaction mixture was refluxed overnight. The solvent was removed under reduced pressure and the residue was taken up in EtOAc and was washed with water and dried (MgSO$_4$). The solvent was removed under reduced pressure and the residue was chromatographed (silica gel, 5% methanol/CH$_2$Cl$_2$) to give the amine 1J as a white solid (197 mg, 43%). ESI m/z: 868 (M−H$^-$).

1 To a solution of 1J (1.33 g, 1.52 mmol) in methanol (100 mL) was added palladium hydroxide on carbon (20%, 375 mg) and the reaction mixture was charged with hydrogen. After stirring 6 h, the mixture was filtered through Celite® and the solvent was removed under reduced pressure to give the phosphate mono-ester 1 as a white solid. ESI m/z: 748 (M−H$^-$).

UTILITY

The compounds of formula I are expected to possess HIV protease inhibitory activity after administration and removal of the phosphate groups and are therefore useful as antiviral agents for the treatment of HIV infection and associated diseases. Following administration, the phosphate group is expected to be removed by chemical or enzymatic processes thereby releasing the active hydroxy-agent.

Dosage and Formulation

The antiviral compounds of this invention can be administered as treatment for viral infections by any means that produces contact of the active agent with the agent's site of action, i.e., the viral protease, in the body of a mammal. They can be administered by any conventional means available for use in conjunction with pharmaceuticals, either as individual therapeutic agents or in a combination of therapeutic agents. They can be administered alone, but preferably are administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to about 1000 milligrams per kilogram of body weight, with the preferred dose being about 0.1 to about 30 mg/kg.

Dosage forms of compositions suitable for administration contain from about 1 mg to about 100 mg of active ingredient per unit. In these pharmaceutical compositions the active ingredient will ordinarily be present in an amount of about 0.5–95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in *Remington's Pharmaceutical Sciences*, supra, a standard reference text in this field.

Useful pharmaceutical dosage-forms for administration of the compounds of this invention can be illustrated as follows:

Capsules

A large number of unit capsules can be prepared by filling standard two-piece hard gelatin capsules each with 100 mg of powdered active ingredient, 150 mg of lactose, 50 mg of cellulose, and 6 mg magnesium stearic.

Soft Gelatin Capsules

A mixture of active ingredient in a digestible oil such as soybean oil, cottonseed oil or olive oil can be prepared and injected by means of a positive displacement pump into gelatin to form soft gelatin capsules containing 100 mg of the active ingredient. The capsules should then be washed and dried.

Tablets

A large number of tablets can be prepared by conventional procedures so that the dosage unit is 100 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

Suspension

An aqueous suspension can be prepared for oral administration so that each 5 mL contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection can be prepared by stirring 1.5% by weight of active ingredient in 10% by volume propylene glycol and water. The solution is sterilized by commonly used techniques.

Combination of components (a) and (b)

Each therapeutic agent component of this invention can independently be in any dosage form, such as those described above, and can also be administered in various ways, as described above. In the following description component (b) is to be understood to represent one or more agents as described previously. Thus, if components (a) and (b) are to be treated the same or independently, each agent of component (b) may also be treated the same or independently.

Components (a) and (b) of the present invention may be formulated together, in a single dosage unit (that is, combined together in one capsule, tablet, powder, or liquid, etc.) as a combination product. When component (a) and (b) are not formulated together in a single dosage unit, the component (a) may be administered at the same time as component (b) or in any order; for example component (a) of this invention may be administered first, followed by administration of component (b), or they may be administered in the reverse order. If component (b) contains more that one agent, e.g., one RT inhibitor and one protease inhibitor, these agents may be administered together or in any order. When not administered at the same time, preferably the administration of component (a) and (b) occurs less than about one hour apart. Preferably, the route of administration of component (a) and (b) is oral. The terms oral agent, oral inhibitor, oral compound, or the like, as used herein, denote compounds that may be orally administered. Although it is preferable that component (a) and component (b) both be administered by the same route (that is, for example, both orally) or dosage form, if desired, they may each be administered by different routes (that is, for example, one component of the combination product may be administered orally, and another component may be administered intravenously) or dosage forms.

As is appreciated by a medical practitioner skilled in the art, the dosage of the combination therapy of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

The proper dosage of components (a) and (b) of the present invention will be readily ascertainable by a medical practitioner skilled in the art, based upon the present disclosure. By way of general guidance, typically a daily dosage may be about 100 milligrams to about 1.5 grams of each component. If component (b) represents more than one compound, then typically a daily dosage may be about 100 milligrams to about 1.5 grams of each agent of component (b). By way of general guidance, when the compounds of component (a) and component (b) are administered in combination, the dosage amount of each component may be reduced by about 70–80% relative to the usual dosage of the component when it is administered alone as a single agent for the treatment of HIV infection, in view of the synergistic effect of the combination.

The combination products of this invention may be formulated such that, although the active ingredients are combined in a single dosage unit, the physical contact between the active ingredients is minimized. In order to minimize contact, for example, where the product is orally administered, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose or other appropriate materials as known in the art, in order to further separate the active components. The polymer coating serves to form an additional barrier to interaction with the other component. In each formulation wherein contact is prevented between components (a) and (b) via a coating or some other material, contact may also be prevented between the individual agents of component (b).

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time or concurrently by the same manner, will be readily apparent to those skilled in the art, based on the present disclosure.

Pharmaceutical kits useful for the treatment of HIV infection, which comprise a therapeutically effective amount of a pharmaceutical composition comprising a compound of component (a) and one or more compounds of component (b), in one or more sterile containers, are also within the ambit of the present invention. Sterilization of the container may be carried out using conventional sterilization methodology well known to those skilled in the art. Component (a) and component (b) may be in the same sterile container or in separate sterile containers. The sterile containers of materials may comprise separate containers, or one or more multi-part containers, as desired. Component (a) and component (b), may be separate, or physically combined into a single dosage form or unit as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

Numerous modifications and variations of the present invention are possible in light of the above teachings. It is therefore to be understood that within the scope of the appended claims, the invention may be practiced otherwise than as specifically described herein.

What is claimed is:
1. A compound of formula I:

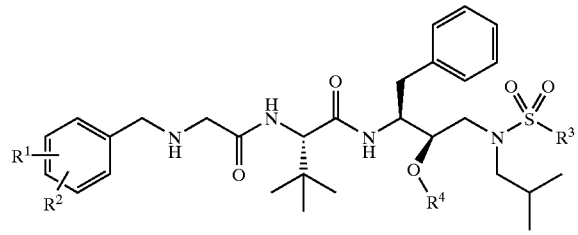

or a pharmaceutically acceptable salt form thereof, wherein:

$R^1$ is F or H;

$R^2$ is F or H; and, $R^3$ is selected from the group: 4-aminophenyl, 3-aminophenyl, 2,3-dihydrobenzofuran-5-yl, and 1,3-benzodioxol-5-yl; and, $R^4$ is selected from the group $PO_3H_2$, $PO_3HNa$, $PO_3HK$, $PO_3Na_2$, and $PO_3K_2$.

2. A compound according to claim 1, wherein the compound is of Formula II:

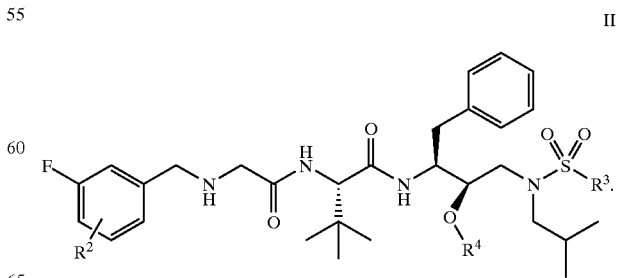

3. A compound according to claim 2, wherein the compound is of Formula IIa:

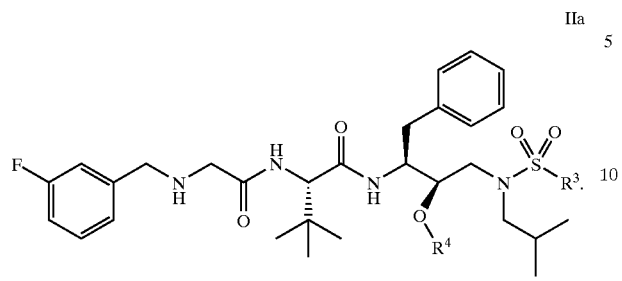

IIa

4. A compound according to claim 3, wherein:
R³ is 3-aminophenyl.
5. A compound according to claim 3, wherein:
R³ is 4-aminophenyl.
6. A compound according to claim 3, wherein:
R³ is 2,3-dihydrobenzofuran-5-yl or 1,3-benzodioxol-5-yl.
7. A compound according to claim 2, wherein the compound is of Formula IIb:

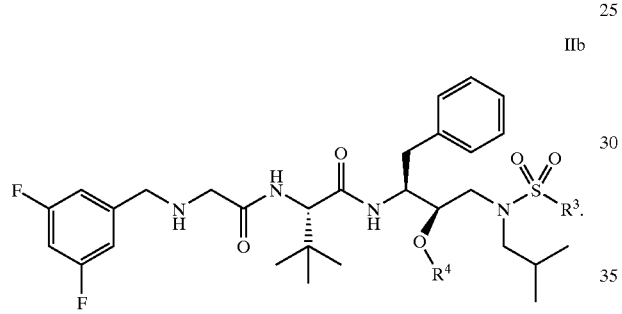

IIb

8. A compound according to claim 7, wherein:
R³ is 3-aminophenyl.
9. A compound according to claim 7, wherein:
R³ is 4-aminophenyl.
10. A compound according to claim 7, wherein:
R³ is 2,3-dihydrobenzofuran-5-yl or 1,3-benzodioxol-5-yl.
11. A compound according to claim 2, wherein the compound is of Formula IIc:

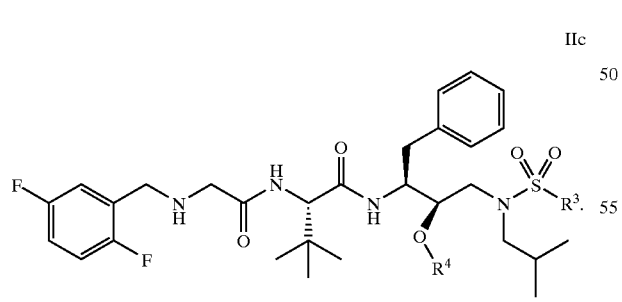

IIc

12. A compound according to claim 11, wherein:
R³ is 3-aminophenyl.
13. A compound according to claim 11, wherein:
R³ is 4-aminophenyl.
14. A compound according to claim 11, wherein:
R³ is 2,3-dihydrobenzofuran-5-yl or 1,3-benzodioxol-5-yl.

15. A compound according to claim 1, wherein the compound is of Formula III:

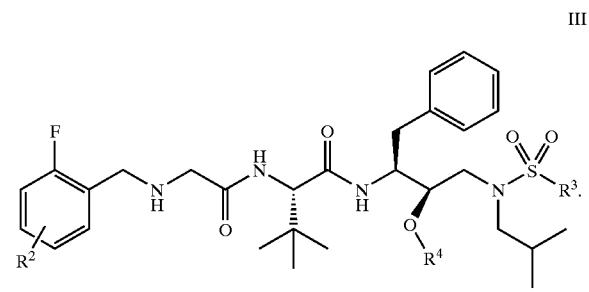

III

16. A compound according to claim 15, wherein the compound is of Formula IIIa:

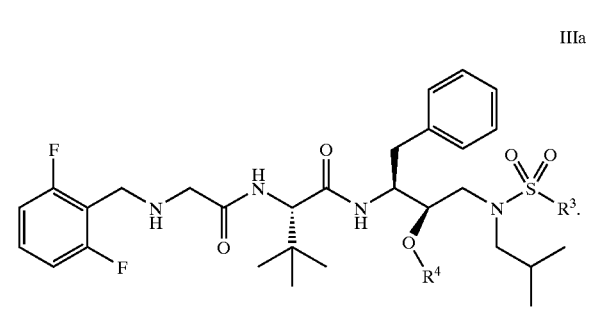

IIIa

17. A compound according to claim 1, wherein the compound is of Formula IV:

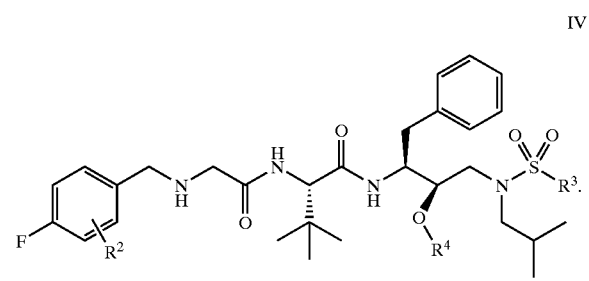

IV

18. A compound according to claim 17, wherein the compound is of Formula IVa:

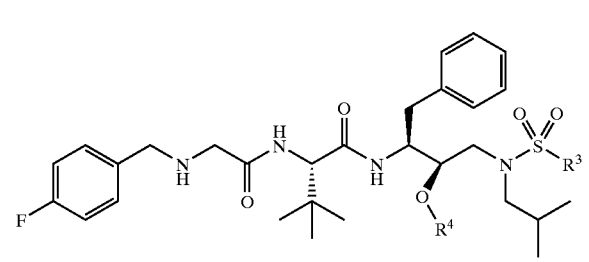

19. A pharmaceutical composition, comprising: a pharmaceutically acceptable carrier and a therapeutically effective amount of a compound according to claim 1.

20. A method for treating HIV infection, comprising: administering to a host in need of such treatment a therapeutically effective amount of a compound according to claim 1, or a pharmaceutically acceptable salt form thereof.

21. A method of treating HIV infection which comprises administering, in combination, to a host in need thereof a therapeutically effective amount of:
  (a) a compound according to claim 1 or stereoisomeric forms, mixtures of stereoisomeric forms, or pharmaceutically acceptable salts thereof; and,
  (b) at least one compound selected from the group consisting of HIV reverse transcriptase inhibitors and HIV protease inhibitors, wherein the HIV reverse transcriptase inhibitors are selected from AZT, ddC, ddI, d4T, 3TC, delavirdine, efavirenz, nevirapine, trovirdine, MKC-442, HBY 097, HBY 1293, ACT, UC-781, UC-782, RD4-2025, and MEN 10979, and wherein the HIV protease inhibitors are selected from saquinavir, ritonavir, indinavir, amprenavir, nelfinavir, palinavir, BMS-232623, GS3333, KNI-413, KNI-272, LG-71350, CGP-61755, PD 173606, PD 177298, PD 178390, PD 178392, tipranavir, DMP-450 and ABT-378.

22. A pharmaceutical composition useful for the treatment of HIV infection, which comprises a therapeutically effective amount of:
  (a) a compound according to claim 1 or pharmaceutically acceptable salts thereof; and,
  (b) at least one compound selected from the group consisting of HIV reverse transcriptase inhibitors and HIV protease inhibitors, in one or more sterile containers, wherein the HIV reverse transcriptase inhibitors are selected from AZT, ddC, ddI, d4T, 3TC, delavirdine, efavirenz, nevirapine, trovirdine, MKC-442, HBY 097, HBY 1293, ACT, UC-781, UC-782, RD4-2025, and MEN 10979, and wherein the HIV protease inhibitors are selected from saquinavir, ritonavir, indinavir, amprenavir, nelfinavir, palinavir, BMS-232623, GS3333, KNI-413, KNI-272, LG-71350, CGP-61755, PD 173606, PD 177298, PD 178390, PD 178392, tipranavir, DMP-450 and ABT-378.

23. A pharmaceutical composition useful for the treatment of HIV infection, wherein the reverse transcriptase inhibitor is selected from the group AZT, efavirenz, and 3TC and the protease inhibitor is selected from the group saquinavir, ritonavir, nelfinavir, and indinavir.

24. A pharmaceutical composition useful for the treatment of HIV infection, wherein the reverse transcriptase inhibitor is AZT.

25. A pharmaceutical composition useful for the treatment of HIV infection, wherein the protease inhibitor is ritonavir.

26. A method according to claim 21, wherein the reverse transcriptase inhibitor is selected from AZT, efavirenz, and 3TC and the protease inhibitor is selected from saquinavir, nelfinavir, ritonavir, and indinavir.

27. A method according to claim 26, wherein the reverse transcriptase inhibitor is AZT.

28. A method according to claim 27, wherein the protease inhibitor is ritonavir.

29. A method according to claim 21, wherein component (b) is a HIV reverse transcriptase inhibitor and a HIV protease inhibitor.

30. A method according to claim 21, wherein component (b) is two different HIV reverse transcriptase inhibitors.

* * * * *